United States Patent [19]

Burns

[11] Patent Number: 4,932,081
[45] Date of Patent: Jun. 12, 1990

[54] SPUTUM CUP
[75] Inventor: James A. Burns, Elizabeth, N.J.
[73] Assignee: Becton, Dickinson and Company, Franklin Lakes, N.J.
[21] Appl. No.: 393,340
[22] Filed: Aug. 11, 1989
[51] Int. Cl.$^5$ .............................................. A61J 19/00
[52] U.S. Cl. ...................................... 4/258; 128/760; 206/569; 422/102; 435/296; 435/30
[58] Field of Search ........................ 4/258, 285, 144.1; 206/569, 446; 128/760, 763; 422/102; 53/490, 363, 317, 331.5, 287; 435/296, 30

[56] References Cited

U.S. PATENT DOCUMENTS

| | | | |
|---|---|---|---|
| 2,218,002 | 10/1940 | Hamilton | 4/258 |
| 3,518,164 | 4/1967 | Andelin et al. | 435/30 |
| 4,244,920 | 1/1981 | Manschot et al. | 422/102 |
| 4,283,498 | 8/1981 | Schlesinger | 435/296 |
| 4,335,730 | 6/1982 | Griffin | 128/760 |
| 4,589,548 | 5/1986 | Fay | 206/363 |
| 4,741,346 | 5/1988 | Wong et al. | 128/760 |
| 4,761,379 | 8/1988 | Williams et al. | 435/296 |

FOREIGN PATENT DOCUMENTS 1215706  3/1986  U.S.S.R. .................................. 4/258

Primary Examiner—Henry J. Recla
Assistant Examiner—Glenn T. Barrett
Attorney, Agent, or Firm—Robert P. Grindle

[57] ABSTRACT

A system is provided for easing the placement of the final screw cap onto a sputum collection container so as to avoid dropping the cap or spilling the specimen in the container onto the hands of the user. An opening is provided in the side wall of the outer protective body of the system so as to gain access to the cap held wedged therein. The wedging action holds the screw cap in place while the user rotates the specimen container to cause cooperation between the screw threads of the screw cap and the associated sputum collection container.

3 Claims, 3 Drawing Sheets

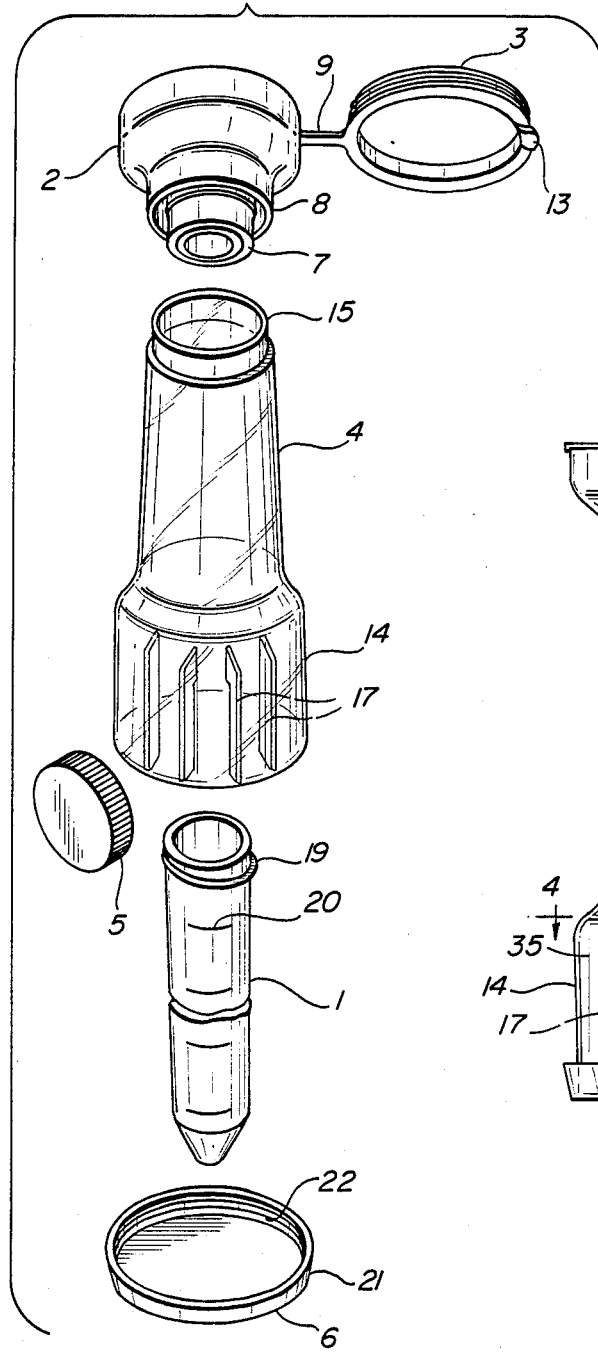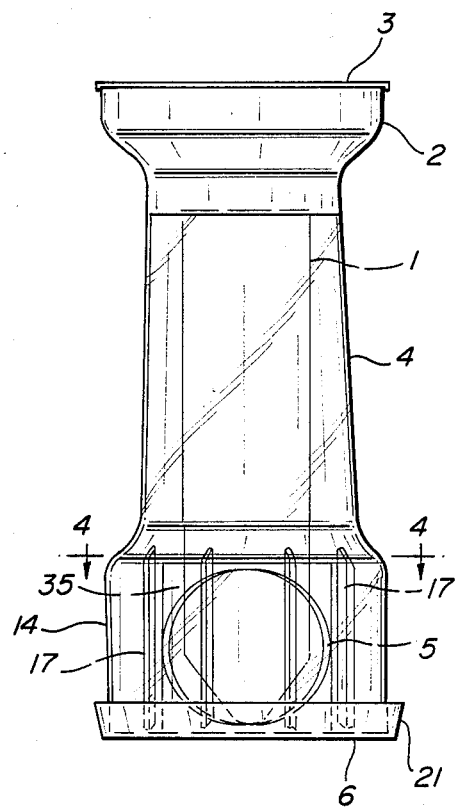

SPUTUM CUP

BACKGROUND AND STATEMENT OF THE INVENTION

This invention relates generally to a system for collecting sputum specimens. More particularly, this invention relates to an arrangement wherein the finally collected specimen in a specimen container may be properly confined in that container by the placement of a screw cap on the open top of the container in a manner obviating dropping the cap or spilling the specimen on the hands of the user.

The system of the invention here includes the combination of an outer shield arrangement which is positioned coaxially around the specimen tube itself, which outer shield provides segregation of the specimen container and the funnel arrangement for receiving the specimen from the hands of the user, until the specimen has been collected in the container. Thereafter, the shield is utilized to hold the screw cap for the specimen container in a fixed position while the specimen container is rotated in order that the cooperating helical threads on the container and the cap therefor may be engaged to hold the cap firmly in place on the container.

Arrangements have been provided in the past for accomplishing what is provided for in the invention here. However, such arrangements have certain limitations which have not overcome the problems of prior art devices. The primary problem is the dropping or losing the cap for the specimen container, once the specimen is in the container. This distracts the clinician or nurse in attempting to place the cap in place over and cover completely the specimen so that the clinician or user is not contaminated by the specimen.

For example, U.S. Pat. No. 4,741,346 provides an arrangement wherein a screw cap is fixed on the base support of the outer circumferential enclosure. Thus, once a specimen collection has been made, the base support is removed and the cap, which is fixed on the support, is re-oriented so that the cap may be screwed down onto the top of the specimen container. One of the problems with such an arrangement is that the cap comes lose from the base support on many occasions during the movement or action in removing the base support from the outer shield or enclosure. When this happens, of course, the cap becomes contaminated. Also, the user may be distracted and spill some of the specimen during such an accidental movement.

Another prior art structure of the kind to which this invention is directed is shown and described in U.S. Pat. No. 4,283,498. In that patent, an arrangement or system is provided which has no outer circumferential shield. Instead, the device is packaged in a flexible outer covering. The cap is taped to the specimen collection container. As will be understood, the cap must be removed from the container by removing the tape which may cause contamination of the cap, as will be understood by practitioners-in-the-art. Of course, the mere activity in attempting to remove or untape the screw cap may cause the cap to be dropped.

U.S. Pat. No. 4,761,379 teaches a screw cap placed under the openable base of the specimen collection system described. In this connection, the cap, again, is wedged in a support underneath the base covering. The cap is not attached to the base support itself. Therefore, the base is not used as a device for screwing the cap on the specimen container. Instead, the specimen container is manipulated to screw the wedged cap onto the top of the specimen container. However, again, this arrangement may cause the cap to drop from the system during the maneuver necessary for placing the cap on the specimen container, if the cap is not properly wedged prior to removal of the base support for exposing the cap for the covering operation.

It should be noted that the last two patents discussed above do not include separate coaxially positioned outer shields for containing the specimen container internally. This has proved to be a somewhat undesirable deficiency by clinical laboratory technicians who object to having to handle the very narrow specimen containers during the course of taking the specimen from a patient who may be in a prone position or not sufficiently alert to place the specimen precisely as provided in the funnel arrangement. The outer shield protects the clinical technician to a degree not provided for with the other arrangements, as discussed above.

U.S. Pat. No. 3,518,164 included a coaxial shield and a cap wedged into the base thereof. However, awkward position is required of the specimen container, as shown in FIG. 3 of that patent to obtain connection between the specimen container and the cap.

With this invention, the wedged cap remains in an untouched position, shielded from any accidental movements until such time as it is engaged to be screwed onto the top of the specimen container.

Other objects and advantages of this invention will be apparent from the following description, the accompanying drawings and the appended claims.

DESCRIPTION OF THE DRAWINGS

FIG. 1 is an exploded perspective view of a sputum collection system embodying this invention;

FIG. 2 is a side elevational view of the sputum collection system of FIG. 1 in assembled form;

Figure 3B:
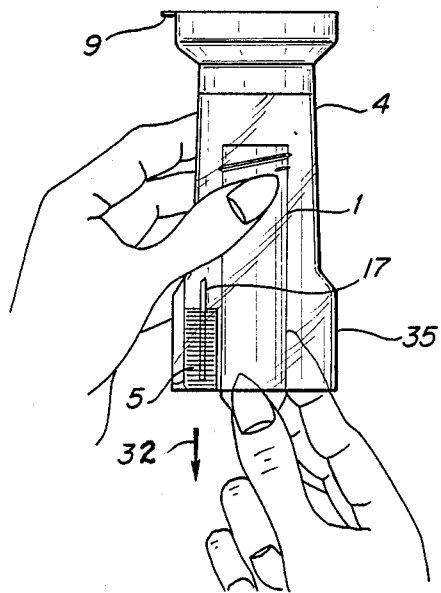
FIGS. 3a, 3b and 3c are side elevational views of the sputum collection system of FIG. 2 showing in a sequence the movements required to utilize the particular cap placement arrangement of the sputum collection system of this invention.

Referring to the drawings in which like reference characters refer to like parts throughout the several views thereof, a graduated elongated specimen receptacle 1, is provided, supported in a outer protective columnar body or shield 4 having a funnel 2 and a hinged funnel cover 3. A screw cap 5 is positioned in the base section 14 of the body 4, as will be described in more detail below. Also provided is a base cover 6 for body 4.

Located on the under surface of funnel 2 are concentric annular rings 7 and 8 which simultaneously frictionally engage the internal specimen container 1, and the outer shield 4. With this arrangement, annular ring 7 communicates with the inner surface of funnel 2 and is adopted to be received within the open end of specimen container 1 to prevent contamination in transfer to the top edge of the receptacle 1. Thus, the unit is designed so that sputum goes directly from funnel 2 into specimen container 1 with no retention of sputum in the funnel or contact of sputum with the rim of the specimen container 1. Both rings 7 and 8 frictionally engage the specimen container and shield 4 to form pressure seals and rigidly maintain the specimen container and protective shield in a fixed coaxial relationship. A cap 3 is provided for the funnel 2 and is attached thereto by a flexible hinge connection 9. Cap 3 has surfaces 10, 12 which serve to pressure seal cap 3 into the upper rim of funnel 2. A finger tab 13 facilitates opening and closing cap 3 from funnel 2.

Figure 4:
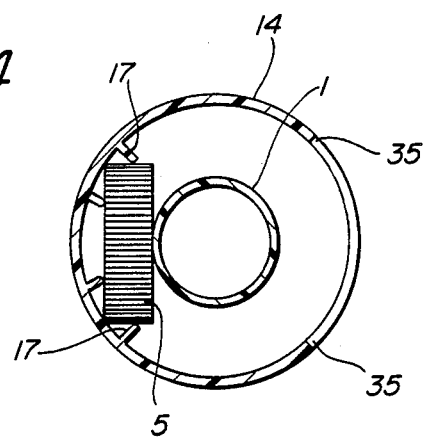
FIG. 4 is a sectional view taken along lines 4—4 of FIG. 2.
Figure 5:
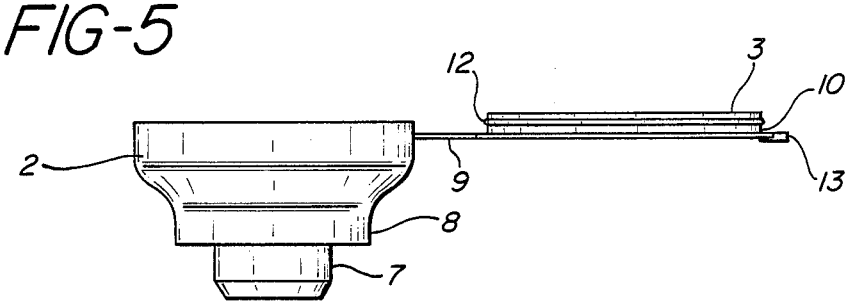
FIG. 5 is a side elevational view of the funnel and funnel cover assembly of the sputum collection system of the invention.

The outer shield 4 comprises an annular column flared at its base 14. The upper edge is indented to form a rim 15 which is seated within annular ring 8 on the under surface of funnel 2. Within flared base 14 of body 4 are four ribs 17 formed against the inner surface and adapted to hold screw cap 5 wedged inside the surface, as shown in FIG. 4.

This invention includes a deliberately placed opening 35 positioned diametrically opposite wedged cap 5, so that in an appropriate positioning of container 1 and shield 4, as discussed below, cap 5 may be readily engaged by the open end of container 1 and screwed tight upon container 1 with no involved manipulation. Prior to this procedure, cap 5 is not in an exposed position to be knocked loose and dropped.

Container 1 is closed at its bottom and open at the top so that the annular rim 7 of funnel 2 may be frictionally seated therein. On the outer surface of the upper edge of container 1 is a thread 19 to engage the inner thread of cap 5. Also, container 1 includes a graduated scale 20 to indicate the quantity of specimen being handled. By shape, structure and size, container 1 is adapted to be used as a centrifuge tube, if required.

Figure 6:
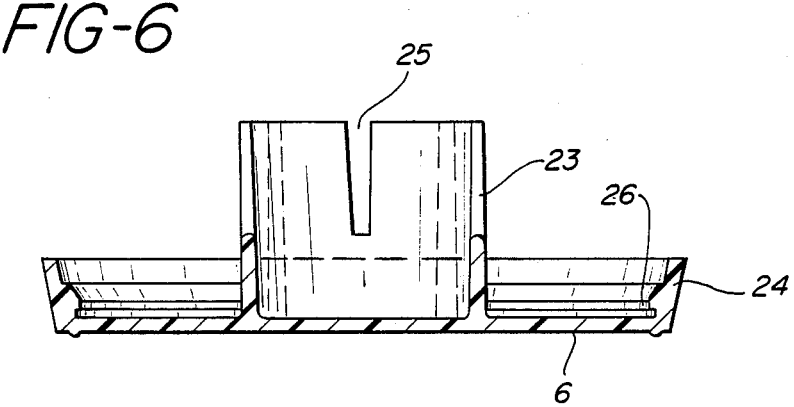
FIG. 6 is a cross-sectional view of the preferred embodiment of a base cap of the system of the invention.

One embodiment of base cover 6 for covering the lower open end of outer shield 4 is shown in FIG. 6 and includes an internal annular ring 23 positioned concentrically in outer rim 24 and projecting upward at a greater height than rim 24. The projection 23 provides support for container 1 when the sputum collection system of the invention is assembled. Moreover, projection 23 is a holder for the specimen container 1 when the cover therefor is removed. Indentations 25 are adapted to permit pressure expansion of projections 23 so that specimen container 1 may be securely held therein. In this connection, as is clearly shown in FIGS. 1 and 2, container 1 includes a conically shaped closed bottom end for cooperating with the projection 23. Rim 24 includes an annular projection 26 for cooperating with the outer circumferential edge of flared base 14 to provide a sealed pressure closure of the assembly.

As will be understood, the entire assembled sputum collection system of the invention may be packaged in a transparent synthetic bag to maintain the system sanitary prior to use.

In the use of the assembled invention as shown in FIGS. 1 and 2, the system is removed from the bag in which it is packaged. A label may be supplied within the bag and pertinent information relating to the patient may be filled out and the label adhered to the outer surface of outer protective shield 4. The hinged funnel lid 3 may then be lifted by means of finger tab 13 for collecting sputum in the container 1 via funnel 2. When a sufficient volume of specimen has been accumulated in container 1, cap 3 may be replaced on the top of funnel 2 and base 6 removed from the bottom surface of shield 4.

Figure 3A:
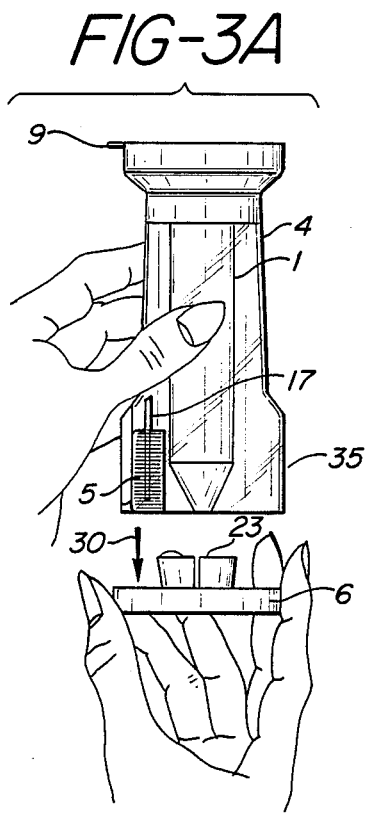
Figure 3C:
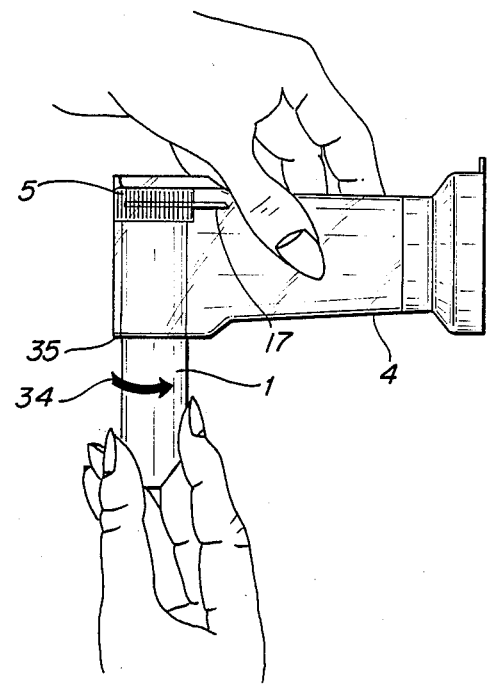

In this connection, a sequence of movements are shown in FIGS. 3a, 3b and 3c. Referring to FIG. 3a, the view shows base cap 6 being removed in the direction of arrow 30. At this time, an referring to FIG. 3b, the technician rasps the sputum collection container 1 in one hand and the shield 4 in the other hand. The sputum container 1 is moved in the direction of arrow 32 to remove it from its coaxial position in shield 4. Subsequently, as shown in FIG. 3c, shield 4 is moved ninety degrees to the position shown in FIG 3c. In this orientated position, the open end or top of container 1 may be moved through opening 35 in the side of the base portion 14 of shield 4 so that the screw threads 19 on the upper outer surface of container 1 may cooperate with the internal screw threads, not shown, of cap 5 for locking cap 5 in place on the top of container 1. This movement is, as will be understood, in the direction of arrow 34.

As will be understood by practitioners-in-the-art, cap 5 is maintained in a fixed position between two cooperating ribs 17 in the bottom of the flared base portion 14 of the outer protective cover 4. Moreover, until such time as cap 5 is engaged, it is not exposed to any opening area for it to fall out of or be knocked by some inadvertent movement prior to the time, when it is engaged by its associated container for capping container 1 in a sealing engagement to protect the specimen and the user from contamination.

The collected specimen is then ready for transfer to a laboratory and may be mailed, if required, in a suitable double mailing container. The container may be constructed of materials such as polypropylene, which provides sufficient structural properties so that the container may be centrifuged to speeds up to 3500 r.p.m. Thus, a specimen can be collected and transported to the laboratory and then tested without personnel touching any of the contaminated parts.

The various parts comprising the sputum collection system of the invention may be manufactured from inexpensive plastic or other synthetic materials of various densities and structural properties which may be subsequently discarded and incinerated once they have been used.

While the forms of apparatus herein described constitute preferred embodiments of the invention, it is to be understood that the invention is not limited to these precise forms of apparatus and that changes may be made therein without departing from the scope of the invention which is defined in the appended claims.

What is claimed is:

1. A sputum collection system comprising
  (a) an elongated specimen container with an open end and a closed end;
  (b) a funnel having a mouth and a discharge end;
  (c) said discharge end of said funnel for engaging said open end of said specimen container;
  (d) an elongated substantially cylindrical shield mounted coaxially around said specimen container having a top end, a bottom end and a side wall;
  (e) said shield being open at the top end for receiving and supporting said funnel, and open at the bottom end;
  (f) a cap for covering said open end of said specimen container;
  (g) cooperating screw threads on said cap and said open end of said specimen container;

(h) an opening in said side wall of said shield adjacent said open bottom end thereof, and positioned on one side of the axis of said shield;
(i) means for holding said cap in wedged orientation on said side wall of said shield diametrically opposite said opening, said holding means holding said cooperating screw threads on said cap toward said opening; and
(j) a base closure for closing the bottom end of said shield;
(k) whereby removal of said base closure allows removal of said specimen container from the open bottom end of said shield so that said shield may be oriented to receive said open end of said specimen container through said opening so that said cooperating screw threads may fix said cap on said open end of said specimen container.

2. The system of claim 1, in which said base closure includes
(a) an inner annular projection adapted to engage said closed end of said specimen container; and
(b) said inner annular projection supporting said specimen container coaxially in said shield for taking a specimen.

3. A shield for expediting the collection of a sputum sample without contaminating the user or the sample; comprising
(a) an elongated substantially cylindrical shield body;
(b) said shield body having an open top end, an open bottom end and a side wall;
(c) a cap with screw threads for use in closing a specimen container positioned in said shield;
(d) an opening in said side wall of said shield adjacent said open bottom end of said shield body; and
(e) means for holding said cap in wedged orientation on said side wall of said shield diametrically opposite said opening, said holding means holding said cap screw threads on said cap toward said opening;
(f) whereby orienting said shield opening adjacent the top of a sputum collection container allows access of a sputum collection container top to said wedged cap.

* * * * *